Figure 1B:
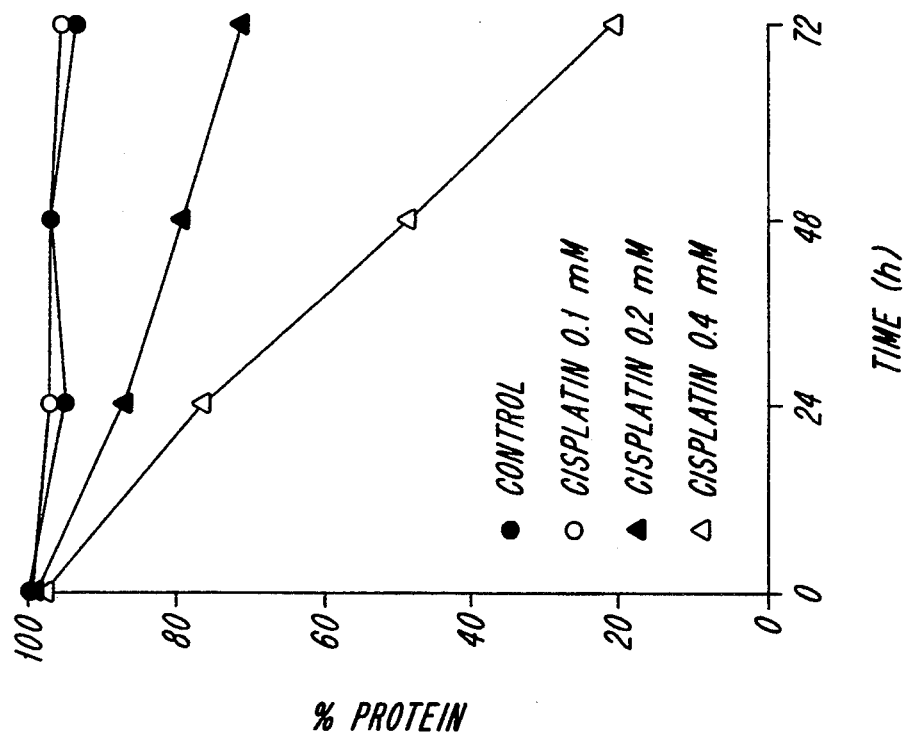

United States Patent [19]

Baldew et al.

[11] Patent Number: 5,385,726

[45] Date of Patent: Jan. 31, 1995

[54] USE OF 2-PHENYL-1,2-BENZISOSELENAZOL-3-(2H)-ONE

[75] Inventors: Glenn S. Baldew, Den Haag; N. P. E. Vermeulen, Leiden, both of Netherlands

[73] Assignee: Rhone-Poulenc Rorer GmbH, Cologne, Germany

[21] Appl. No.: 89,306

[22] Filed: Jul. 12, 1993

Related U.S. Application Data

[63] Continuation of Ser. No. 46,253, Apr. 6, 1993, abandoned.

[30] Foreign Application Priority Data

Aug. 6, 1990 [DE] Germany .............. 4024885

[51] Int. Cl.$^6$ .............. A61K 49/00; A61K 33/24; A61K 31/33
[52] U.S. Cl. .............. 424/10; 424/649; 514/183
[58] Field of Search .............. 424/10, 649; 514/183

[56] References Cited

U.S. PATENT DOCUMENTS

| | | | |
|---|---|---|---|
| 4,352,799 | 10/1982 | Renson et al. | 514/183 |
| 4,757,063 | 7/1988 | Parnham | 514/183 |
| 4,784,994 | 11/1988 | Romer et al. | 514/183 |

Primary Examiner—Jerome D. Goldberg
Attorney, Agent, or Firm—Burns, Doane, Swecker & Mathis

[57] ABSTRACT

2-Phenyl-1,2-benzisoselenazol-3(2H)-one(Ebselen) is capable of reducing the cisplatin-induced nephrotoxicity and neurotoxcity during cytostatic treatment.

16 Claims, 3 Drawing Sheets

USE OF 2-PHENYL-1,2-BENZISOSELENAZOL-3-(2H)-ONE

This application is a continuation of U.S. Ser. No. 08/046,253, filed Apr. 6, 1993, now abandoned which is a continuation of PCT/EP91/01438, filed Jul. 31, 1991, which designated the United States.

The invention concerns a new use for 2-phenyl-1,2-benzisoselenazol-3(2H)-one (Ebselen) for the treatment and prophylaxis of the side effects that can be caused by medicinal administration of cisplatin and of pharmaceutical preparations containing this drug and the application of Ebselen for the manufacture of medicinal preparations for the treatment of the side effects that can occur on medicinal treatment with cisplatin, or for prophylaxis against them.

2-Phenyl-1,2-benzisoselenazol-3(2H)-one is a known compound that can be used for the treatment of rheumatism (DE-OS 30 27 073) or for the treatment of oxidative stress (DE-OS 36 16 923). The compound can be prepared, for example, by the reaction of 2-methylseleno-N-phenyl-benzamide with phosphorus pentachloride followed by hydrolysis according to the method of M. Renson and R. Weber (Bulletin de la Soc. Chim. de France 1976 (7/8), p. 1124–1126).

Cisplatin is a cytostatic often used in cancer therapy for the treatment of many different types of tumor. The medicament is highly effective for the treatment of various solid tumors, such as cancer of the tests, ovaries, bladder, head and neck and "non-small cell" lung cancer.

However, its clinical application is frequently exceedingly difficult, since its mechanism of action does not only affect pathological cells but healthy cells as well, thus causing damage to the body.

These side effects most frequently manifest themselves in the form of a (gradual) renal intoxication, intoxication of the gastrointestinal tract, of the peripheral nerves and of the bone marrow (deposition of platinum).

The occurrence of nephrotoxicity and/or neurotoxicity is most frequent.

The neurotoxicity is a further serious and clinically relevant side effect. On chronic administration it manifests itself in the form of primary sensory neuropathy, retrobulbar neuritis and neurosensory deafness.

There have been many attempts to compensate for or minimize these negative side effects of cisplatin administration.

Thus, various derivatives of cisplatin have been found to produce fewer undesirable side effects, but the actual cytotoxic effect of the administered substance is considerably reduced in parallel.

In the past some substances, such as sodium thiosulfate (L. E. Pfeifle et al., J. Clin. Oncol. 3 (1987), p. 237–244) and diethyl dithiocarbamate (D. L. Bodenner et al., Cancer Res. 46 (1986), p. 2751–2755), have been tested for ability to protect healthy cells from the effects of cisplatin. These substance do provide a certain degree of protection against the nephrotoxic and/or neurotoxic effects of cisplatin, but their clinical application is limited by the fact that thiosulfate reduces the pharmacodynamic efficacy of cisplatin; this phenomenon does not occur with diethyl dithiocarbamate, but the substance is very toxic.

It is already known that simple selenium compounds—sodium diselenite for instance—are able to reduce cisplatin-induced nephrotoxicity in mice without reducing the tumor-inhibiting activity of cisplatin (J. P. Berry et al., Cancer Res. 44 (1984) 2864–2868 and Baldew et al., Cancer Res. 49 (1989) 3020–3023, amongst others). However, the high potential toxicity of selenium prohibits human clinical applications.

The object of the present invention is to provide a drug that inhibits or obviates the side effects of medicinal administration of cisplatin itself.

Surprisingly it was found that this purpose can be achieved by administering cisplatin together with 2-phenyl-1,2-benzisoselenazol-3(2H)-one (Ebselen).

The object of the invention is achieved by the use of 2-phenyl-1,2-benzisoselenazol-3(3H)-one for the manufacture of medicaments for the treatment and prophylaxis of the side-effects occurring on the medicinal administration of cisplatin.

The administration of cisplatin with Ebselen leads to an appreciable diminution in the side effects produced by cisplatin; a practically complete inhibition was observed in the case of the nephrotoxicity and/or neurotoxicity induced by cisplatin.

Ebselen can be administered simultaneously with cisplatin, but administration over a period extending from 1 hour before and after the administration of cisplatin does not diminish the effect of Ebselen.

In a preferred embodiment a combination of cisplatin with Ebselen is used for the manufacture of medicaments for the treatment of neoplastic diseases and prophylaxis of the side-effects occurring on the medicinal administration of Cisplatin, comprising of 10 mg to 100 mg Cisplatin and 10 mg to 2000 mg Ebselen. Preferably the combination is in the form of a medical kit of the two active ingredients comprising collection or package containing the two agents in separate but adjacent form for the use according to the present invention.

Since, in contrast to the previously known and applied selenium compounds, Ebselen is low in toxicity (LD0 > 1000 mg/kg body weight in acute investigations in mice and rats) and the maximum doses to be administered lie greatly below this value, administration to patients can be regarded as being without danger.

Cisplatin-induced nephrotoxicity

The influence of Ebselen on cisplatin-induced toxic effects could be proven in two different methodological approaches:
1) in an in-vitro investigation in a cell line which expresses many of the characteristics of proximal tubular cells
2) in-vivo in mice subject to a tumor-inducing treatment.

The aim of the investigations was to get information on the influence of Ebselen on the cisplatin side-effects as well as on the antitumor potency of the drug.

1) Influence on in-vitro toxicity of cisplatin in LLC-PK$_1$ cells

LLC-PK$_1$ are porcine kidney cells which express many characteristics of proximal tubule epithelium. The LLC-PK$_1$ cell has been used to study the nephrotoxicity of cisplatin. In this cell line the LDH-leakage can be used as criterium for cell toxicity.

Material and Methods

LLC-PK$_1$ cells were obtained from Flow Labatories, Zwanenburg, The Netherlands and maintained by serial passages in 75-cm$^2$ plastic culture flasks in an atomosphere of 5% $CO_2$ −95% air at 37° C. The complete medium consisted of E 199 medium (Flow laboratories), supplemented with 2 mM L-Glutamine and 5% Fetal Calf Serum. Cells were seeded in 24 well culture dishes (0.2 cm$^2$/well) and allowed to grow to confluence (2.4×10$^5$ cell/cm$^2$) over 8 days in serum containing 5% fetal calf serum. The cells were then maintained in serum-free medium for 2 days before drug treatment. Only monolayers in which dome formation occurred were used for the experiments.

Cisplatin was dissolved in a sterile salt solution (114 mM NaCl, 5.4 mM KCl, 0.8 mM MgCl$_2$, 1.2 mM CaCl$_2$, 0.8 mM Na$_2$H PO$_4$, 0.2 mM NaH$_2$PO$_4$, 16 mM NaHCO$_3$, 5.5 mM glucose), saturated with 5% CO$_2$ −95% air at 37° C. (pH 7.4). Ebselen was dissolved in 2% dimethylsulfoxide in the sterile salt solution.

Monolayers of LLC-PK$_1$ were lysed with trypsin and cell viability was assessed by measuring LDH activity, according to the method of Stevens et al. (J. Biol. Chem., (1986) 261: 3325-3332), and by measuring the amount of protein remaining attached to the culture plate with bovine serum albumine as standard, according to the method of Lowry et al. (J. Biol. Chem., (1951) 193: 265-275).

Monolayers of LLC-PK$_1$ cells were washed twice with physiological saline and then exposed to cisplatin or ebselen for 60 min. After incubation, the monolayers were washed 3 times with physiological saline to remove residual drug. Subsequently, the cells were grown in medium containing 5% fetal calf serum. Cell viability was assessed at different timepoints. In control experiments, monolayers were exposed to the vehicle in stead of drugs.

The influence of ebselen on the cytotoxicity of cisplatin in LLC-PK$_1$ cells was estimated by washing monolayers of LLC-PK$_1$ cells twice with physiological saline and incubation with ebselen for 60 min. Subsequently, monolayers were washed 3 times with physiological saline and incubated with cisplatin as described above. In control experiments, ebselen was replaced by the vehicle.

Results

Cytotoxicity of cisplatin in LLC-PK$_1$ cells.

The influence of cisplatin at several concentrations on the viability of LLC-PK$_1$ cells is shown in FIG. 1.

Figure 1A:
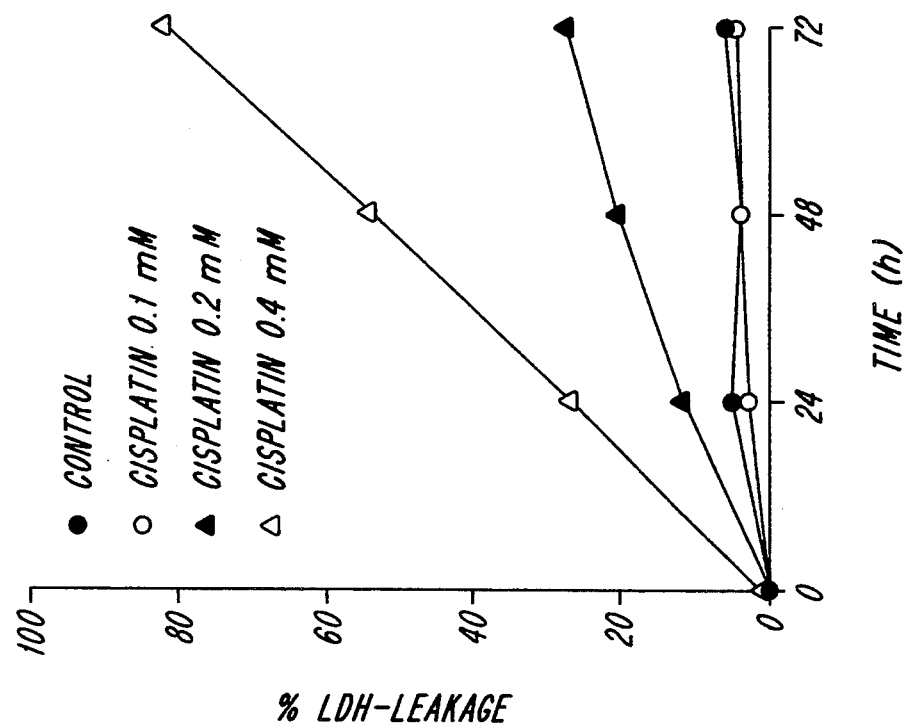

FIGS. 1(a) and 1(b) show cytotoxicity of cisplatin in LLC-PK$_1$ cells. Quiescent cells were exposed to cisplatin for 1 h, washed and then incubated in freh medium until assayed for viability by measuring LDH-leakage (A) and the amount of protein remaining attached to the culture plate (B). Data represent one typical example out of three independent experiments. SD<6%.

Measurements of LDH and of the amount of protein remaining attached to the culture plate, yielded similar results. Exposure of the quiescent cells to a cisplatin concentration of 0.4 mM during 1 h, followed by maintainance of the cells in drug free medium, caused a decrease in cell viability, which was first observed 24 h after termination of the incubation with cisplatin. Cell viability was further reduced to 21% in the next 48 h. Under these conditions, a cisplatin concentration of 0.1 mM did not significantly reduce the cell viability, measured up to 72 h after exposure.

Exposure of the LLC-PK$_1$ cells to Ebselen, 5-15 uM, for 1 h did not alter their viability as measured by the leakage of intracellular LDH in the medium and by the amount of protein remaining attached to the culture plate, up till 72 h after exposure.

The influence of Ebselen on the cytotoxicity of cisplatin in LLC-PK$_1$ cells.

The results presented in FIG. 2 demonstrate that pre-incubation of the LLC-PK$_1$ cells with Ebselen, 5-15 uM for 1 h, protected the cells from a decrease in viability induced by exposure of the cells to 0.2 or 0.4 mM cisplatin.

Figure 2B:
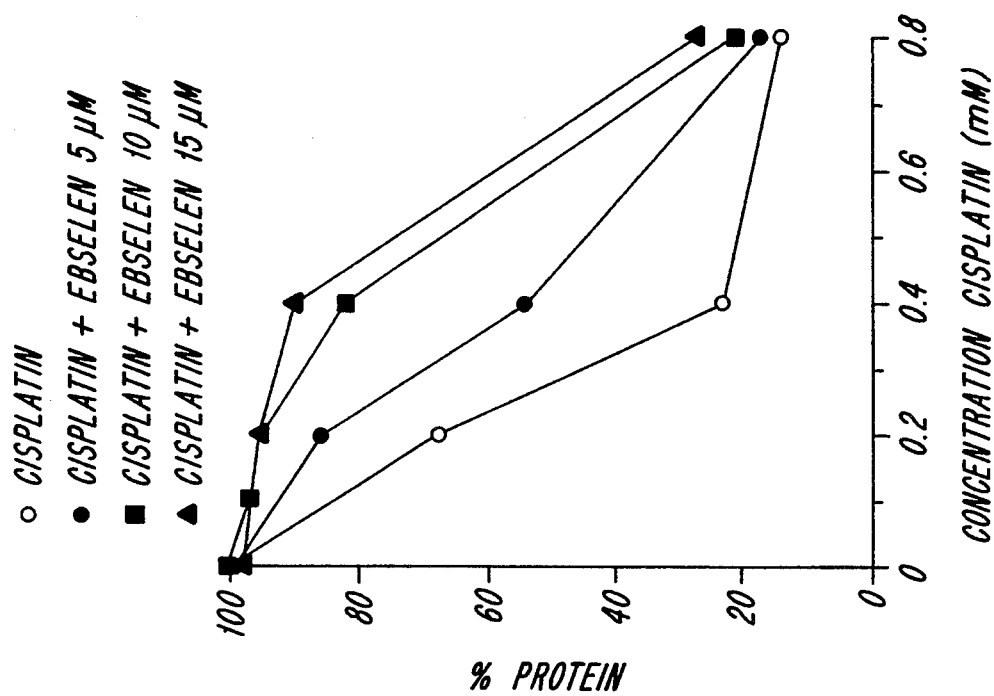
Figure 2A:
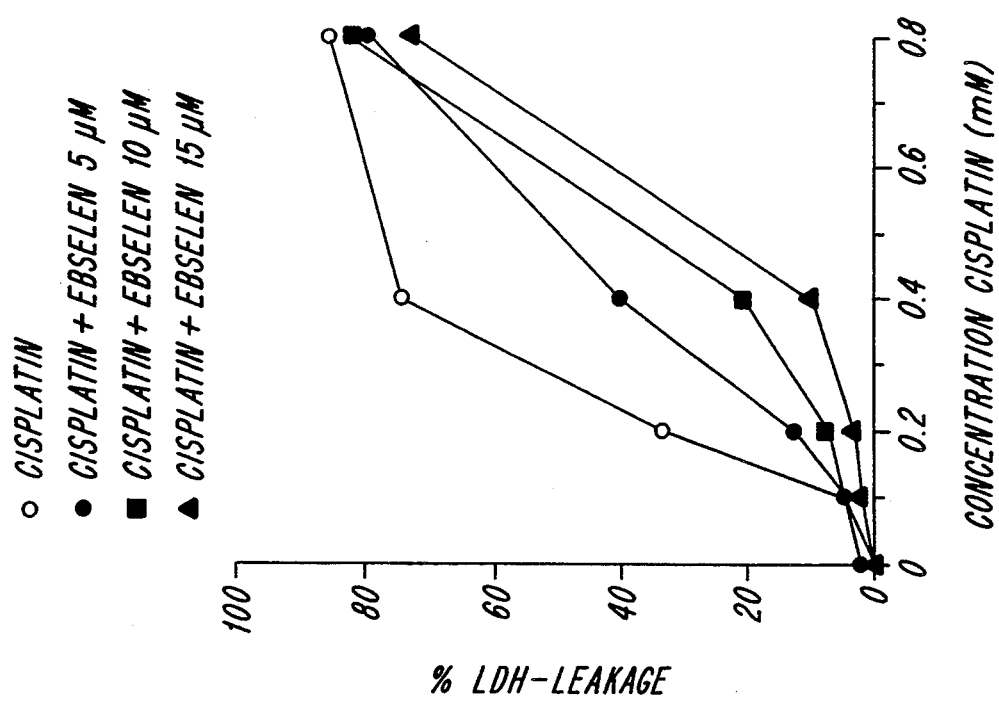

FIGS. 2(a) and 2(b) show the the influence of ebselen on the cytoxicity of cisplatin in LLC-PK$_1$. Quiescent cells were exposed to ebselen for 1 h, washed exposed to cisplatin for 1 h, washed and then incubated in fresh medium until assayed (t=72 h) for viability by measuring LDH-leakage (A) and the amount of protein remaining attached to the culture plate (B). Data represent one typical example out of three independent experiments. SD<6%.

The protective effect of Ebselen was concentration-dependent: the highest protection was obtained at an ebselen concentration of 15 uM.

Pre-incubation of ebselen could not protect the cells against the decrease in viability caused by exposure to a cisplatin concentration of 0.8 mM for 1 h.

Figure 3B:
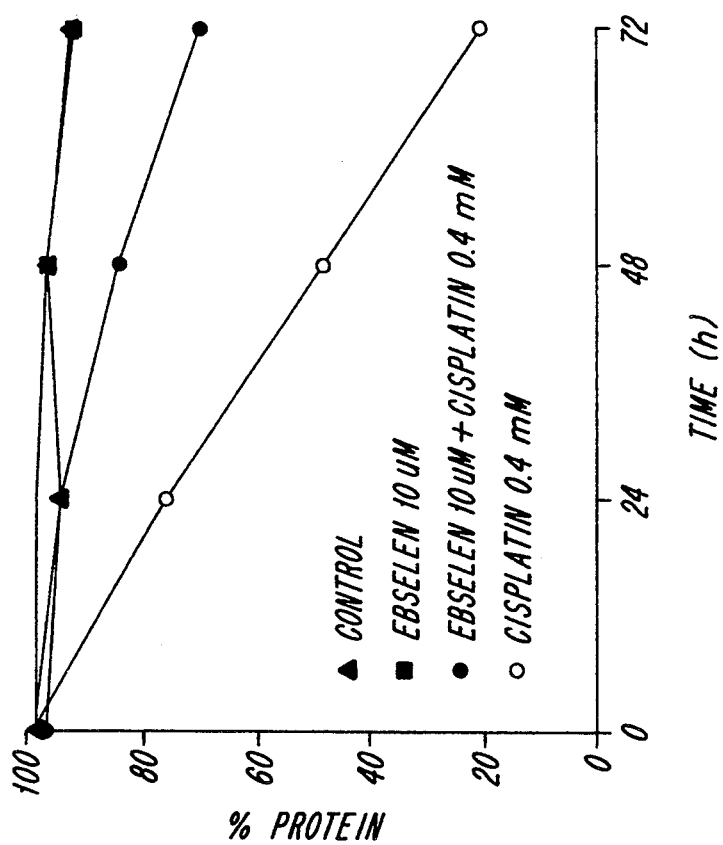

The protective effect of Ebselen as function of the time after exposure to cisplatin is plotted in FIG. 3.

Figure 3A:
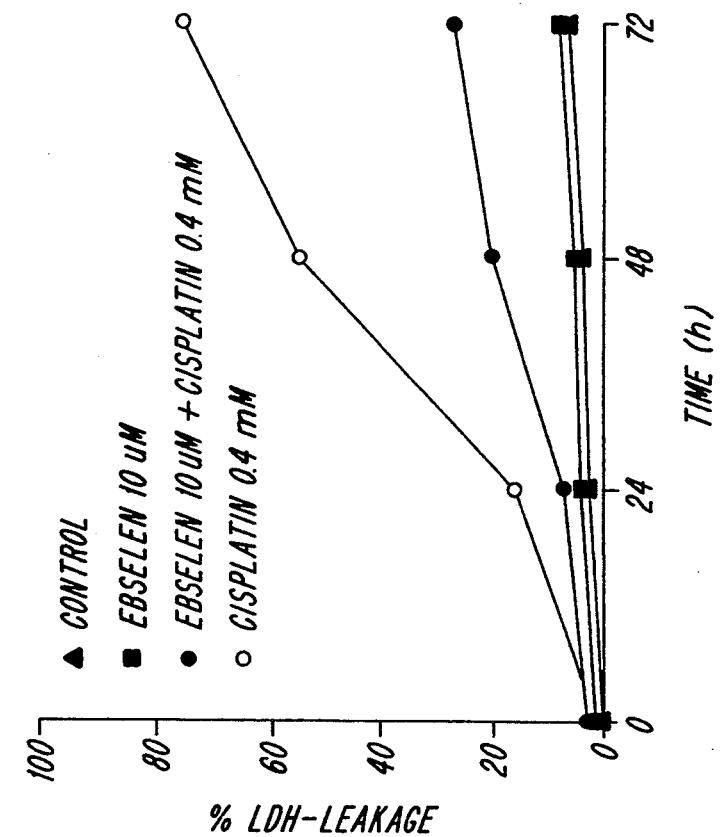

FIGS. 3(a) and (b) show the time course of the protective effect of ebselen on the cytotoxicity of cisplatin in LLC-PK$_1$ cells. Quiescent cells were exposed to 10 uM ebselen for 1 h, washed, exposed to 0.4 mM cisplatin for 1 h, washed and then incubated in fresh medium until assayed for viability by measuring LDH-leakage (A) and the amount of protein remaining attached to the culture plate (B). Data represent one typical example out of three independent experiments. SD<6%.

As shown, the viability of the cells, measured after exposure to 0.4 mM cisplatin for 1 h, was during the whole period (up till 72 h exposure) significantly higher in cells which were pre-exposed to 10 uM Ebselen for 1 h.

2) Influence on in-vivo toxicity of cisplatin in mice

Tumors. MPC 11 tumor cells were obtained from the institute of Pathology, University of Utrecht, The Netherlands. The MPC 11 tumor originated as a plasmacytoma, and was originally obtained from Dr. D. Catty, Birmingham, United Kingdom. The tumor cells were maintained by weekly passages in BALB/c mice. Freshly harvested ascitic cells were used in the experiments. Cells were counted with a hemocytometer. Transplantable Prima mammary tumor cells were obtained from the Radiobiological Institute TNO, Rijswijk, The Netherlands. The Prima tumor originated as a mammary carcinoma, induced by forced breeding in BALB/c mice bearing murine mammary tumor virus. The Prima tumor cell-line was cultured in vitro in standard Dulbecco's modification of Minimal Essential Medium (Gibco, Paisley, United Kingdom), supplemented with L-glutamine (500 mg/l), 2-mercaptoethanol (60 umol/l) and 10% fetal calf serum (Flow Laboratories, Zwanenburg, The Netherlands).

Laboratory Animals. Female BALB/c mice were obtained from the Central Institute for the Breeding of Laboratory Animals/Harlan Sprague-Dawley (CPB/HSD), Zeist, The Netherlands. The mice were 8 weeks of age and weighed 18-20 g at the start of the experiments. All animals were provided with standard laboratory food (SRMA chow, Hope Farms, Woerden, The Netherlands) and water ad libitum.

Treatment. Animals were divided at random into groups of 8. Cisplatin was administered in 1.0 ml physiological saline. Ebselen was dissolved in a mixture of dimethylsulfoxide/polyethyleneglycol/physiological saline (1/4/20) and administered i.p. in a volume of 0.6 ml.

Kidney Function. The influence of Ebselen on cisplatin-induced nephrotoxicity was studied by injection of ebselen i.p. 1 h prior to or 1 h after cisplatin administration. Control groups were treated with Ebselen or the vehicle. Blood samples were obtained from the retroorbital venous plexus in the mice. Serum creatinine and BUN were measured daily in pilot studies (data not shown) and in more extensive studies at the time of maximally observed toxicity: Day 4.

Liver Function. Serum glutamic pyruvate transaminase (SGPT) and SGOT were determined on Days 1 and 4 after treatment with cisplatin or ebselen and cisplatin. Control groups were treated with ebselen or the vehicle.

Histology. Mice were sacrificed four days after treatment with cisplatin alone or Ebselen and cisplatin. Control groups were treated with Ebselen alone or the vehicle. Kidneys and livers were removed and processed for light microscopy. Sections of 6 um thickness were cut and stained in hematoxylin:eosin. All slides were examined without prior knowledge of the treatment given to the animal from which the specimen under investigation was taken.

Evaluation of Antitumor Activity. The influence of ebselen on the antitumor activity of cisplatin against an ascitic tumor was examined in BALB/c mice, i.p. inoculated with $10^6$ MPC tumor cells on Day 0. After 24 h, the mice were treated with a single i.p. dose of cisplatin. The influence of ebselen was assessed by injecting ebselen i.p. 1 h prior to cisplatin. Control groups were treated with ebselen or the vehicle. Mice were examined daily for occurrence of tumors. The experiments were terminated on Day 42 and median survival times (MSTs) were calculated.

BALB/c mice, inoculated with $0.5 \times 10^6$ Prima tumor cells s.c. in the left thigh (Day 0), were used to investigate the effect of Ebselen on the antitumor activity of cisplatin against solid tumors. One group of mice was treated with a single i.p. dose of cisplatin 24 h after inoculation of tumor cells. Another group was treated with a single i.p. injection of ebselen 1 h before cisplatin. Control groups were treated with ebselen or the vehicle. The occurrance of tumors was examined daily by palpation. The experiments were terminated on Day 15 when the tumors were excised and weighed.

Statistics. Student's test, unpaired, was used to evaluate the significance of differences between experimental groups. The level of significance was set at $P<0.05$.

Results

Toxicity of Ebselen. It could be demonstrated that ebselen itself did not cause functional liver- or kidney-damage in BALB/c mice.

The influence of Ebselen on nephrotoxicity of cisplatin. The data in Table 1 demonstrate a dose-dependent protective effect of ebselen against cisplatin-induced nephrotoxicity in mice. Maximal protection was obtained with an ebselen dose of 10.0 mg/kg. The results, summarized in Table 2, demonstrate a protective effect of ebselen against nephrotoxicity induced by various cisplatin doses in mice.

Administration of cisplatin in a dose range of 11.5 to 19.0 mg/kg increased levels of BUN and serum creatinine at Day 4 posttreatment. Administration of Ebselen 1 h before cisplatin prevented the increase in levels of BUN and serum creatinine at all cisplatin doses tested with exception of the highest dose. When ebselen was administered 1 h after cisplatin, a protective effect against cisplatin-induced elevations of the levels of BUN and serum creatinine was also observed, but less marked.

The protective effect of Ebselen against cisplatin-induced kidney damage, as observed by BUN and creatinine levels, was confirmed by histology. The tubules of the kidneys of mice treated with Ebselen, 10 mg/kg and 1 h thereafter with cisplatin showed considerably less degeneration and less cell loss of the tubular epithelium at Day 4 posttreatment than those of mice treated with cisplatin alone.

Retroperitoneal ganglionic-tissue attached to the kidneys was also examined histologically. Damage to retroperitoneal ganglionic cells was more pronounced in mice treated with cisplatin alone than in mice treated with cisplatin and ebselen administered 1 h before cisplatin. These observations suggest that ebselen might also be able to provide protection against cisplatin-induced neurotoxicity.

The influence of Ebselen on the antitumor activity of cisplatin. MPC 11 plasmacytoma. The antitumor activities of various cisplatin/ebselen combinations in BALB/c mice, inoculated with MPC 11 tumor cells, are shown in Table 3. Ebselen did not reduce the antitumor activity of cisplatin. Down to cisplatin doses as low as 6.5 mg/kg, no significant differences were observed in median survival time (MST) of mice treated with cisplatin compared with those of mice treated with the corresponding cisplatin dose plus ebselen. Treatment with ebselen alone resulted in a MST identical to that of the control group treated with the vehicle alone.

The data in Table 3 also show that ebselen protects BALB/c mice against cisplatin nephrotoxicity without reducing the efficacy of the drug against the MPC 11 tumor. The mean BUN level of mice inoculated with MPC 11 tumor cells and treated with cisplatin, 13.0 mg/kg, was $162\pm56$ mg/100 ml on Day 5. Four animals of this group (n=8) were dead on Day 7. The surviving animals did not develop tumors (MST>42 days). MST of mice inoculated with $10^6$ MPC 11 cells on Day 0 was 16 days. All mice (n=8) treated with ebselen, 10 mg/kg, and cisplatin 13.0 mg/kg, survived (MST>48 days). These mice did not develop tumors. The mean BUN level of these mice was $29\pm10$ mg/100 ml on Day 5, which is much lower than that of the group treated with cisplatin alone.

Prima tumor. Cisplatin in doses of 9.0 and 11.5 mg/kg was effective against the Prima mammary tumor in BALB/c mice (Table 4). Ebselen (10 mg/kg) was not effective against the Prima tumor and did not reduce the antitumor activity of cisplatin.

The data in Table 4 also show that ebselen reduced the nephrotoxicity but not the antitumor activity of cisplatin in Prima tumor bearing mice. Mice (n=8) treated with cisplatin alone, 13.0 mg/kg, showed highly elevated BUN-levels (mean: $148\pm85$ mg/100 ml) on Day 5, but the animals survived. None of the mice of this group had tumors as assessed by palpation on Day 7. On the other hand, none of the mice treated with ebselen and cisplatin showed kidney damage. All mice survived and none of them had tumors. Neither BUN levels on Day 5 nor mean tumor weight on Day 15 of mice treated with ebselen alone were significantly different from those of the control group, treated with the vehicle alone.

TABLE 1

The influence of various ebselen doses on the nephrotoxicity of cisplatin in BALB/c mice

| Cisplatin (mg/kg) | Ebselen[a] (mg/kg) | BUN (mg/100 ml) | Creatinine (mg/100 ml) |
|---|---|---|---|
| 0[b] | 0 | 22 ± 2[c] | 0.54 ± 0.03 |
| 0 | 10.0 | 21 ± 3 | 0.53 ± 0.03 |
| 14.5 | 0 | 184 ± 33 | 5.9 ± 0.6 |
| 14.5 | 2.5 | 154 ± 59 | 5.4 ± 0.7 |
| 14.5 | 5.0 | 105 ± 20[d] | 3.0 ± 1.0[d] |
| 14.5 | 7.5 | 72 ± 17[d] | 1.7 ± 0.4[d] |
| 14.5 | 10.0 | 37 ± 10[d] | 0.73 ± 0.07[d] |
| 14.5 | 12.5 | 44 ± 18[d] | 0.69 ± 0.08[d] |

[a]Ebselen was administered i.p. 1 h before cisplatin
[b]Control animals were injected with the vehicle
[c]Mean ± (n = 8)
[d]$p < 0.05$ compared to the groups, treated with cisplatin alone

TABLE 2

The influence of ebselen on the nephrotoxicity of various cisplatin doses in BALB/c mice

| Cisplatin (mg/kg) | Ebselen (mg/kg) | BUN (mg/100 ml) | Creatinine (mg/100 ml) |
|---|---|---|---|
| 0[a] | 0 | 20 ± 2[b] | 0.53 ± 0.03[b] |
| 0 | 10.0[c] | 19 ± 3 | 0.53 ± 0.02 |
| 11.5 | 0 | 70 ± 42 | 1.6 ± 0.6 |
| 11.5 | 10.0[c] | 22 ± 5[d] | 0.54 ± 0.04[d] |
| 13.0 | 0 | 130 ± 38 | 4.5 ± 1.0 |
| 13.0 | 10.0[c] | 40 ± 27[d] | 0.83 ± 0.05[d] |
| 13.0 | 10.0[e] | 67 ± 23[d] | 1.5 ± 0.3[d] |
| 14.5 | 0 | 175 ± 52 | 5.8 ± 0.7 |
| 14.5 | 10.0[c] | 57 ± 16[d] | 1.2 ± 0.3[d] |
| 14.5 | 10.0[e] | 102 ± 22[d] | 2.8 ± 0.3[d] |
| 16.0 | 0 | 232 ± 40 | 6.4 ± 1.0 |
| 16.0 | 10.0[c] | 108 ± 55[d] | 3.2 ± 0.6[d] |
| 19.0 | 0 | 275 ± 26 | 6.9 ± 0.2 |
| 19.0 | 10.0[c] | 133 ± 70[d] | 4.5 ± 0.8[d] |

[a]Control animals were injected with the vehicle
[b]Mean ± SD (n = 8)
[c]Ebselen was given before cisplatin
[d]$p < 0.05$ compared to the groups, treated with cisplatin alone
[e]Ebselen was given 1 h after cisplatin

TABLE 3

The influence of ebselen on the nephrotoxicity and antitumor activity of cisplatin in BALB/c mice inoculated with MPC 11 tumor cells (n = 8)

| Cisplatin (mg/kg) | Ebselen[a] (mg/kg) | BUN (mg/100 ml) | Survival Day 7 (%) | Incidence of tumors Day 7 (%) | MST (days) | T/C[b] % |
|---|---|---|---|---|---|---|
| 0 | 0 | 22 ± 1[c] | 100 | 100 | 16 ± 3 | 100 |
| 0 | 10.0 | 20 ± 2 | 100 | 100 | 17 ± 2 | 106 |
| 4.0 | 0 | 22 ± 2 | 100 | 100 | 24 ± 4 | 150 |
| 4.0 | 10.0 | 20 ± 2 | 100 | 100 | 23 ± 5 | 144 |
| 6.5 | 0 | 23 ± 3 | 100 | 100 | 29 ± 4 | 181 |
| 6.5 | 10.0 | 22 ± 2 | 100 | 100 | 30 ± 2 | 188 |
| 9.0 | 0 | 21 ± 2 | 100 | 0 | >30 | >300 |
| 9.0 | 10.0 | 23 ± 2 | 100 | 0 | >48 | >300 |
| 11.5 | 0 | 86 ± 32 | 87.5[d] | 0 | >48 | >300 |
| 11.5 | 10.0 | 24 ± 3[e] | 100 | 0 | >48 | >300 |
| 13.0 | 0 | 162 ± 56 | 50[d] | 0 | >48 | >300 |
| 13.0 | 10.0 | 29 ± 10[e] | 100 | 0 | >48 | >300 |
| 14.5 | 0 | 204 ± 32 | 0 | 0 | | |
| 14.5 | 10.0 | 79 ± 46[e] | 75[d] | 0 | >48 | >300 |

[a]Ebselen was given 1 h before cisplatin
[b]T/C = MST treated/MST control
[c]Mean ± SD
[d]Mice alive at Day 7 did not develop tumors as judged by daily examination and by autopsy on Day 48. Mice, dead on Day 7 were presumed to have died from cisplatin toxicity
[e]$p < 0.05$ compared to the groups treated with cisplatin alone

TABLE 4

The influence of ebselen on the nephrotoxicity and antitumor activity of cisplatin in BALB/c mice inoculated with Prima breast tumor cells (n = 8).

| Cisplatin (mg/kg) | Ebselen[a] (mg/kg) | BUN Day 5 (mg/100 ml) | Survival Day 8 (%) | Incidence of tumors Day 8[c] (%) | Mean tumor weight Day 15 (g) | T/C[b] Day 15 (%) |
|---|---|---|---|---|---|---|
| 0 | 0 | 21 ± 1[d] | 100 | 100 | 1.5 ± 0.3 | |
| 0 | 10.0 | 22 ± 1 | 100 | 100 | 1.5 ± 0.4 | 100 |
| 6.5 | 0 | 22 ± 1 | 100 | 100 | 1.4 ± 0.2 | 93 |
| 6.5 | 10.0 | 23 ± 2 | 100 | 100 | 1.4 ± 0.4 | 93 |
| 9.0 | 0 | 22 ± 2 | 100 | 0 | 0.7 ± 0.4 | 47 |
| 9.0 | 10.0 | 23 ± 2 | 100 | 0 | 0.8 ± 0.4 | 53 |
| 11.5 | 0 | 62 ± 23 | 100 | 0 | 0.42 ± 0.08 | 28 |
| 11.5 | 10.0 | 22 ± 2[a] | 100 | 0 | 0.38 ± 0.06 | 25 |
| 13.0 | 0 | 148 ± 85 | 100 | 0 | 0.12 ± 0.02 | 8 |
| 13.0 | 10.0 | 22 ± 3[a] | 100 | 0 | 0.12 ± 0.03 | 8 |
| 14.5 | 0 | 215 ± 34 | 0 | 0 | | 7 |
| 14.5 | 10.0 | 93 ± 77[a] | 75 | 0 | 0.11 ± 0.02 | 7 |

[a]Ebselen was given 1 h before cisplatin
[b]T/C = mean tumor weight treated mice/mean tumor weight control mice.
[c]Incidence of tumors was assessed by palpation
[d]Mean ± SD
[e]$p < 0.05$ compared to the groups treated with cisplatin alone The above experiments make it evident that ebselen can be a valuable prophylactic and/or therapeutic for the nephrotoxicity and/or neurotoxicity induced by cisplatin.

For prophylactic or pharmaceutical application in the case of side effects caused by medicinal treatment using cisplatin, Ebselen is administered orally or parenterally in a suitable dosage form at dose levels of 10 to 2000 mg per day, preferably 10 to 300 mg per day in one or several separate doses, preferably two to three doses per day.

Parenteral administration can take place according to the method described in DE-AS 38 26 892.

This present investigation applies to pharmaceutical preparations containing Ebselen as active engredient. The preparations involved are such as are intended for enteral, i.e. oral or rectal, or parenteral administration in which the drug is present alone or in combination with the usual pharmaceutical excipients.

The pharmaceutical preparation of the drug preferably takes the form of individual doses, adjusted to the desired administration, e.g. tablets, sugarcoated tablets, capsules, suppositories, granules, solutions, emulsions or suspensions. The usual dose of the substances is between 10 and 2000 mg per day, preferably between 10 and 300 mg per day and can be administered in the form of one dose or several doses, preferably two to three doses per day. The manufacture of the medicaments according to the invention is further illustrated in the following examples.

EXAMPLE 1

Tablets

| | |
|---|---|
| 2-Phenyl-1,2-benzisoselenazol-3(2H)-one | 30 mg |
| Lactose | 150 mg |
| Crystalline cellulose | 50 mg |
| Calcium carboxymethylcellulose | 7 mg |
| Magnesium stearate | 3 mg |

The substances listed are mixed and pressed according to the usual methods, if required the pressings can be coated in the usual manner.

EXAMPLE 2

Tablets

| | |
|---|---|
| 2-Phenyl-1,2-benzisoselenazol-3(2H)-one | 50 mg |
| Microcrystalline cellulose | 150 mg |
| Cutina ® HR | 15 mg |
| Hydroxypropylmethylcellulose phthalate | 20 mg |

EXAMPLE 3

Capsules

| | |
|---|---|
| 2-Phenyl-1,2-benzisoselenazol-3(2H)-one | 30 mg |
| Lactose | 102 mg |
| Crystalline cellulose | 56 mg |
| Colloidal silicon dioxide | 2 mg |

The substances listed are mixed and granulated by the usual methods and filled into hard gelatine capsules.

EXAMPLE 4

Capsules

| | |
|---|---|
| 2-Phenyl-1,2-benzisoselenazol-3(2H)-one | 50 mg |
| Talc | 5 mg |
| Aerosil 200 | 10 mg |

We claim:

1. A method for the prevention or treatment of a side effect resulting from the administration of cisplatin, said method comprising administering an effective amount of 2-phenyl-1,2-benzisoselenazol-3(2H)-one to a mammal in need of the prevention or treatment of a side effect of cisplatin and a pharmaceutically acceptable carrier therefor.

2. The method as claimed in claim 1, wherein said cisplatin and said 2-phenyl-1,2-benzisoselenazol-3(2H)-one are administered at approximately the same time.

3. The method as claimed in claim 1, wherein said 2-phenyl-1,2-benzisoselenazol-3(2H)-one is administered one hour before to one hour after the administration of cisplatin.

4. The method as claimed in claim 1, wherein the amount of said cisplatin is 10 mg to 100 mg per day and the amount of said 2-phenyl-1,2-benzisoselenazol-3(2H)-one is 10 mg to 2000 mg per day.

5. The method as claimed in claim 1, wherein the amount of said 2-phenyl-1,2-benzisoselenazol-3(2H)-one is administered 10 to 300 mg per day.

6. The method as claimed in claim 1, wherein said 2-phenyl-1,2-benzisoselenazol-3(2H)-one is administered enterally.

7. The method as claimed in claim 6, wherein said 2-phenyl-1,2-benzisoselenazol-3(2H)-one is administered orally.

8. The method as claimed in claim 1, wherein said 2-phenyl-1,2-benzisoselenazol-3(2H)-one is administered parenterally.

9. A method for the prevention or treatment of the nephrotoxicity or neurotoxicity resulting from the administration of cisplatin, said method comprising administering an effective amount of 2-phenyl-1,2-benzisoselenazol-3(2H)-one to a mammal in need of the prevention or treatment of the nephrotoxicity or neurotoxicity of cisplatin and a pharmaceutically acceptable carrier therefore.

10. The method as claimed in claim 9, wherein said cisplatin and said 2-phenyl-1,2-benzisoselenazol-3(2H)-one are administered at approximately the same time.

11. The method as claimed in claim 9, wherein said 2-phenyl-1,2-benzisoselenazol-3(2H)-one is administered one hour before to one hour after the administration of cisplatin.

12. The method as claimed in claim 9, wherein the amount of said cisplatin is 10 mg to 100 mg per day and the amount of said 2-phenyl-1,2-benzisoselenazol-3(2H)-one is 10 mg to 2000 mg per day.

13. The method as claimed in claim 9, wherein the amount of said 2-phenyl-1,2-benzisoselenazol-3(2H)-one is administered 10 to 300 mg per day.

14. The method as claimed in claim 9, wherein said 2-phenyl-1,2-benzisoselenazol-3(2H)-one is administered enterally.

15. The method as claimed in claim 14, wherein said 2-phenyl-1,2-benzisoselenazol-3(2H)-one is administered orally.

16. The method as claimed in claim 9, wherein said 2-phenyl-1,2-benzisoselenazol-3(2H)-one is administered parenterally.

* * * * *